US008679346B2

(12) United States Patent
Kagamihara

(10) Patent No.: US 8,679,346 B2
(45) Date of Patent: Mar. 25, 2014

(54) OPTICAL-ISOMER-SEPARATING AGENT

(75) Inventor: Yasuhiro Kagamihara, Hyogo (JP)

(73) Assignee: Daicel Corporation, Sakai-shi, Osaka (JP)

( * ) Notice: Subject to any disclaimer, the term of this patent is extended or adjusted under 35 U.S.C. 154(b) by 253 days.

(21) Appl. No.: 13/199,249

(22) Filed: Aug. 24, 2011

(65) Prior Publication Data

US 2011/0313146 A1 Dec. 22, 2011

Related U.S. Application Data

(63) Continuation of application No. 11/884,417, filed as application No. PCT/JP2006/307259 on Mar. 30, 2006.

(30) Foreign Application Priority Data

Mar. 31, 2005 (JP) ................................. 2005-101846

(51) Int. Cl.
B01D 15/20 (2006.01)
B01D 15/38 (2006.01)
B01D 15/00 (2006.01)
G01N 30/30 (2006.01)

(52) U.S. Cl.
USPC .......... 210/656; 210/198.2; 422/70; 73/61.52

(58) Field of Classification Search
None
See application file for complete search history.

(56) References Cited

U.S. PATENT DOCUMENTS 5,679,572 A * 10/1997 Okamoto et al. ............. 210/656
5,736,259 A * 4/1998 Oda et al. ...................... 428/532
2003/0192829 A1 10/2003 Ohnishi et al.

FOREIGN PATENT DOCUMENTS

| EP | 0 527 235 A1 | 2/1993 |
|---|---|---|
| EP | 0 625 524 A2 | 11/1994 |
| EP | 0 644 204 A1 | 3/1995 |
| EP | 0 699 902 A1 | 3/1996 |
| EP | 0 718 625 A1 | 6/1996 |
| EP | 0 978 498 A1 | 2/2000 |
| EP | 1 422 521 A1 | 5/2004 |
| EP | 1 500 430 A2 | 1/2005 |
| EP | 1 721 664 A1 | 11/2006 |
| JP | 05-255129 | 10/1993 |
| JP | 07-260762 | 10/1995 |
| JP | 08-005623 | 1/1996 |
| JP | 2669554 | 7/1997 |
| JP | 2751004 | 2/1998 |
| JP | 11-510193 | 9/1999 |
| JP | 2004-003935 | 1/2004 |
| WO | WO 95/18833 | 7/1995 |
| WO | WO 97/04011 | 2/1997 |

OTHER PUBLICATIONS

Claessens et al. Characterization of stationary phases for reversed-phase liquid chromatography. Eindhoven: Technische Universiteit Eindhoven (1999) p. 1-291.*

(Continued)

Primary Examiner — Katherine Zalasky
(74) Attorney, Agent, or Firm — Flynn, Thiel, Boutell & Tanis, P.C.

(57) ABSTRACT

An enantiomeric isomer separating agent includes a polysaccharide derivative supported by particles of a support by chemical bonding and has a concentration of eluted component (in terms of mass proportion), as determined through a liquid passing test of 20 ppm or lower.

7 Claims, No Drawings

(56) References Cited

OTHER PUBLICATIONS

"Bonded cellulose-derived high-performance liquid chromatography chiral stationary phases I. Influence of the degree of fixation on selectivity", by C. Minguillon et al, Journal of Chromatography A, vol. 728, 1996, pp. 407-414.

"Benzoates of Cellulose Bonded on Silica Gel: Chiral Discrimination Ability as High-Performance Liquid Chromatography Chiral Stationary Phases", by L. Oliveros et al, Chirality, vol. 9, 1997, pp. 145-149.

"Chitosan derivatives as chiral selectors bonded on allyl silica gel: preparation, characterisation and study of the resulting high-performance liquid chromatography chiral stationary phases", by A. Senso et al, Journal of Chromatography A, vol. 839, 1999, pp. 15-21.

"Solvent versatility of bonded cellulose-derived chiral stationary phases for high-performance liquid chromatography and its consequences in column loadability", by P. Franco et al, Journal of Chromatography, vol. 793, No. 2, Jan. 1998, pp. 239-247.

"Development of chiral stationary phases consisting of low-molecular-weight cellulose derivatives covalently bonded to silica gel", by N. Kasuya et al, Cellulose, vol. 9, 2002, pp. 263-269.

\* cited by examiner

OPTICAL-ISOMER-SEPARATING AGENT

This is a continuation of prior U.S. application Ser. No. 11/884 417, filed Aug. 14, 2007, which was the national stage of International Application No. PCT/JP2006/307259, filed Mar. 30, 2006, which International Application was not published in English.

TECHNICAL FIELD

The present invention relates to an enantiomeric isomer separating agent and a method of producing the agent.

BACKGROUND ARTS

A separating agent obtained by carrying a polysaccharide derivative on silica gel has been generally used as, for example, an enantiomeric resolution agent for high performance liquid chromatography. The manners in which the silica gel supports the polysaccharide derivative are classified into the case where silica gel is caused to support the polysaccharide derivative physically (physical support type separating agent) and the case where silica gel is caused to support the polysaccharide derivative by chemical bonding (chemical support type separating agent). See JP-B-2751004 or JP-A-8-5623.

The chemical support type separating agent has a smaller amount of eluted component originating from the polysaccharide derivative than that of the physical support type separating agent, even when an organic solvent in which the polysaccharide derivative is soluble is used. However, an unreacted polysaccharide derivative is present, even in the chemical support type separating agent, so an eluent contains an eluted component originating from the polysaccharide derivative.

In the case where an eluted component originating from, for example, an unreacted polysaccharide derivative is present in an eluent as described above, the following problem arises depending on whether the amount of eluted component is large or small when a separating agent containing the eluted component is used as a separating agent for high performance liquid chromatography: the stability of the baseline of a chromatogram deteriorates, or the purity of a fractionated product cannot be sufficiently increased.

Investigations have already been conducted on a method reducing the amount of eluted component in the physical support type separating agent. JP-A 7-260762 discloses a coating type separating agent having a small amount of eluted component.

DISCLOSURE OF THE INVENTION

A low-molecular-weight polysaccharide derivative is eluted in a physical support type separating agent. This is because the molecular weight distribution of a polysaccharide to be used varies.

On the other hand, not only the low-molecular-weight polysaccharide derivative described above but also a low-molecular-weight or high-molecular-weight polysaccharide derivative that has not been chemically bonded to a support, and, furthermore, an impurity originating from a compound having a functional group capable of reacting with a hydroxyl group of a polysaccharide derivative are eluted in a chemical support type separating agent. As described above, the eluted component from a chemical support type polysaccharide derivative is different from that of a physical support type polysaccharide derivative.

When a conventional chemical support type separating agent is used for a separating agent for high performance liquid chromatography, as described above, it still needs to be improved in terms of prevention of the deterioration of the stability of the baseline of a chromatogram, the stabilization of the quality of a fractionated product, and an improvement in purity of the fractionated product.

The present invention provides an enantiomeric isomer separating agent improved in the separating performance when it is used for a separating agent of high performance liquid chromatography and a method of producing the agent.

The present invention provides an enantiomeric isomer separating agent, which includes a polysaccharide derivative supported on particles of a support by chemical bonding, and has a concentration of eluted component (in terms of mass proportion) as determined through a liquid passing test under the following conditions of 20 ppm or lower:

(Liquid Passing Test)

(1) the enantiomeric isomer separating agent is packed into a column having a diameter of 1 cm and a length of 25 cm by a slurry method, (2) an organic solvent in which the polysaccharide derivative is soluble is used as a solvent, and passing of the organic solvent whose temperature is set at 40° C. is initiated at a flow rate of 8 ml/min, (3) collection of the organic solvent passed is initiated 1 hour after the initiation of the liquid passing, the organic solvent is collected for 1 hour (480 ml), and a mass (MO of the organic solvent is measured, and (4) the liquid collected is condensed and dried, a mass ($M_2$) of a residue is measured, and the concentration of eluted component is determined from an expression $M_2/M_1$.

According to the present invention, there is provided a method of producing the above-mentioned enantiomeric isomer separating agent, including the steps of: washing an unwashed enantiomeric isomer separating agent with an organic solvent in which the polysaccharide derivative is soluble once or multiple times; and drying the washed enantiomeric isomer separating agent.

Further, according to the present invention, there is provided a method of separating enantiomeric isomers including bringing the enantiomeric isomers into contact with the above-mentioned enantiomeric isomer separating agent, or use of the above enantiomeric isomer separating agent for separating enantiomeric isomers.

DETAILED DESCRIPTION OF THE INVENTION

It should be noted that the term "unwashed enantiomeric isomer separating agent" refers to an enantiomeric isomer separating agent that does not satisfy the following requirement: the concentration of eluted component (in terms of mass proportion) upon performance of a liquid passing test under the above-mentioned conditions is 20 ppm or lower.

An enantiomeric isomer separating agent of the present invention has good separating performance, and can increase the purity of a fractionated enantiomeric isomer. The agent is suitable for high performance liquid chromatography.

(Enantiomeric Isomer Separating Agent)

The enantiomeric isomer separating agent of the present invention has a concentration of eluted component (in terms of mass proportion) as determined through the following liquid passing test of 20 ppm or lower, preferably 15 ppm or lower, or more preferably 10 ppm or lower.

(Liquid Passing Test)

(1) the enantiomeric isomer separating agent is packed into a column having a diameter of 1 cm and a length of 25 cm by a slurry method, (2) an organic solvent in which the polysaccharide derivative is soluble is used as a solvent, and passing of the organic solvent whose temperature is set at 40° C. is initiated at a flow rate of 8 ml/min, (3) collection of the organic solvent passed is initiated 1 hour after the initiation of the liquid passing, the organic solvent is collected for 1 hour (480 ml), and a mass ($M_1$) for each fraction of the organic solvent is measured, and (4) the liquid collected is condensed and dried, a mass ($M_2$) of a residue is measured, and the concentration of eluted component is determined from an expression $M_2/M_1$.

(Method of Producing Enantiomeric Isomer Separating Agent)

First, a chemical support type separating agent is produced by chemically bonding a polysaccharide derivative to a support.

A polysaccharide derivative to be used in the present invention is well known, and can be produced by applying, for example, Examples 1 to 5 of JP-A-2004-3935, a method described in Synthesis Example 1 of JP-A-7-260762, or a method described in Production Method 3 of paragraph 43 of JP-B-2751004.

An enantiomeric isomer separating agent (unwashed enantiomeric isomer separating agent) obtained by causing a support to support the polysaccharide derivative to be used in the present invention is well known, and can be produced by applying, for example, a method described in Example 1 of JP-B-2751004.

A porous organic support or a porous inorganic support can be used as the support, and a porous inorganic support is preferable. A polymeric substance composed of, for example, polystyrene, polyacrylamide, or polyacrylate can be suitably used in a porous organic support. Silica, alumina, magnesia, glass, kaolin, titanium oxide, a silicate, hydroxyapatite, or the like can be suitably used in a porous inorganic support; silica gel is particularly preferable.

It should be noted that, when silica gel is used, silica gel is desirably subjected to a surface treatment such as a silanization treatment (silanization treatment with an aminoalkylsilane) or a plasma treatment in order that an influence of a silanol remaining on the surface of the silica gel may be eliminated, and the affinity of silica gel for an enantiomerically active polymer compound may be improved. However, no problem arises even when the surface of the silica gel is not treated at all.

A porous support, in particular, silica gel has a particle diameter of preferably 1 to 300 μm, more preferably 15 to 100 μm, or still more preferably 20 to 50 μm, and has an average pore diameter of preferably 200 to 8,000 Å, more preferably 200 to 4,000 Å, or still more preferably 300 to 2,000 Å. It should be noted that the particle diameter of the porous support is substantially the particle diameter of the separating agent.

The average pore diameter of the porous support preferably falls within the range because a solution of an enantiomerically active polymer compound is sufficiently infiltrated into the pores of the porous support, and the enantiomerically active polymer compound can easily adhere to the inner wall of each of the pores in a uniform fashion. Further, the pressure loss of the separating agent can be maintained at a low level because the pores are prevented from clogging.

Examples of the polysaccharide conveying polysaccharide derivative include any of a synthetic polysaccharide, a natural polysaccharide, and a natural products-modified polysaccharide as long as the polysaccharide or the derivative thereof is enantiomerically active. However, the polysaccharide or the derivative thereof preferably has a high regularity in bonding manner.

Examples of the polysaccharide include: β-1,4-glucan (cellulose); α-1,4-glucan (amylose or amylopectin); α-1,6-glucan (dextran); β-1,6-glucan (pustulan); β-1,3-glucan (such as curdlan or schizophyllan); α-1,3-glucan; β-1,2-glucan (a Crown Gall polysaccharide); β-1,4-galactan; β-1,4-mannan; α-1,6-mannan; β-1,2-fructan (inulin); β-2,6-fructan (levan); β-1,4-xylan; β-1,3-xylan; β-1,4-chitosan; α-1,4-N-acetylchitosan (chitin); pullulan; agarose; and alginic acid. Starch containing amylose is also included.

Of those, cellulose, amylose, β-1,4-xylan, β-1,4-chitosan, chitin, β-1,4-mannan, inulin, curdlan, and the like are preferred because they easily enable highly pure polysaccharides to be obtained. Cellulose and amylose are particularly preferred.

The number-average degree of polymerization of the polysaccharide (average number of pyranose or furanose rings in one molecule) is preferably 5 or more, or more preferably 10 or more, and has no particular upper limit. However, the number-average degree of polymerization is preferably 1,000 or less in terms of the easiness for handling, and is more preferably 5 to 1,000, still more preferably 10 to 1,000, or particularly preferably 10 to 500.

A product obtained by bonding a compound having a functional group capable of reacting with a hydroxyl group to some or all of the hydroxyl groups of the above-mentioned polysaccharide by, for example, ester bonding, urethane bonding or ether bonding can be used as the polysaccharide derivative.

Examples of functional group-containing compounds that can react with a hydroxyl group include isocyanate derivatives, carboxylic acids, esters, acid halides, acid amide compounds, halide compounds, aldehydes, alcohols or other elimination group-containing compounds; and their aliphatic, alicyclic, aromatic, and heteroaromatic compounds.

Examples of a particularly preferable polysaccharide derivative include a polysaccharide ester derivative and a polysaccharide carbamate derivative.

The term "eluted component" as used in the present invention refers to, for example, a reaction by-product such as an isocyanic acid derivative or carboxylic acid derivative originating from a compound having a functional group capable of reacting with a hydroxyl group, or a polysaccharide derivative that has not been chemically bonded to the support.

Next, the enantiomeric isomer separating agent obtained by chemically bonding the polysaccharide derivative to the support (unwashed enantiomeric isomer separating agent) is washed with an organic solvent in which the polysaccharide derivative is soluble. The washing can be performed once or multiple times (for example, two to ten times).

A method of washing the unwashed separating agent may be any method with which the unwashed separating agent and the organic solvent can be sufficiently brought into contact with each other, and a column mode, a batch mode, a method involving pouring the organic solvent into a residue after filtration to wash the unwashed separating agent, a heating reflux method, or the like is applicable.

Examples of organic solvent used for washing can be any solvent selected from tetrahydrofuran (THF), acetone, ethyl acetate, chloroform, methylene chloride, dimethyl acetoamide, dimethylformamide (DMF), and methanol.

The total used amount of the organic solvent is preferably 5 to 100 ml, more preferably 10 to 70 ml, or still more preferably 20 to 40 ml with respect to 1 g of the polysaccharide derivative in the unwashed separating agent.

Whether the temperature of the organic solvent is lower than the boiling point of the solvent or not lower than the boiling point can be chosen depending on the washing method, and the temperature of the organic solvent is preferably 50 to 150° C., more preferably 60 to 120° C., or still more preferably 70 to 100° C.

The time needed for washing the unwashed separating agent may be any time required to reduce the amount of eluted component to a predetermined amount or less, and is generally about 1 to 100 hours, or preferably about 1 to 50 hours.

A filler after the washing can be recovered by, for example, filtration. The temperature at which the filler is filtrated is typically 10 to 150° C., or preferably 20 to 100° C.

Next, the separating agent after the washing is dried. A method of drying the separating agent is not particularly limited, and is appropriately selected in consideration of the time period for which the separating agent is subjected to a drying treatment, and a cost for the treatment. However, the separating agent is preferably subjected to a drying treatment under a reduced pressure at room temperature to 100° C. for 2 to 24 hours.

An enantiomeric isomer separating agent obtained by the production method of the present invention has a concentration of eluted component in the above-mentioned liquid passing test of a predetermined value or lower. As a result, when the enantiomeric isomer separating agent of the present invention is used as a filler for high performance liquid chromatography to separate enantiomeric isomers, nearly no unreacted polysaccharide derivative is eluted, so the baseline of a chromatogram at the time of fractionation is stabilized, and the purity of a fractionated product can be increased. Accordingly, a high-quality enantiomerically resoluble substance can be stably supplied.

EXAMPLES

Example 1

(i) Synthesis of Amylose-Bonded Silica Gel

Under a nitrogen atmosphere, 100 g of silica gel, the surface of which had been treated with a siliane treatment agent having an amino group at any one of its terminals, and 20 g of amylose were dispersed in 380 ml of DMSO at 70° C. A borane-pyridine complex and acetic acid were added to the dispersion, and the whole was stirred for 20 hours. The stirred mixture was separated by filtration, and the residue was washed with methanol, DMSO, and methanol in the stated order. After that, the residue was dried in a vacuum, whereby amylose-bonded silica gel was obtained.

(ii) Synthesis of enantiomeric isomer separating agent in which hydroxyl group of amylose is turned into 3,5-dimethylphenylcarbamate Under a nitrogen atmosphere, 100 g of amylose-bonded silica gel, 3 g of 4-dimethylaminopyridine, 300 ml of DMF, and 45 g of 3,5-dimethylphenylisocyanate were dispersed, and the dispersion was stirred at 75° C. for 24 hours.

The amylose derivative-bonded silica gel thus obtained was washed with 2.4 L of DMF at 75° C. (24 ml with respect to 1 g of an amylose derivative), whereby a target enantiomeric isomer separating agent was obtained.

(iii) A predetermined liquid passing test was performed by using the enantiomeric isomer separating agent of the present invention and ethyl acetate as a solvent to determine the concentration of eluted component (ppm). As a result, the $M_1$ was 416.08 g, the $M_2$ was 1.2 mg, and the ratio $M_2/M_1$ was 3 ppm.

Example 2

Silica gel, the surface of which had been treated with a silane treatment agent having an amino group at any one of its terminals, was caused to support cellulose tris(3,5-dimethylphenylcarbamate) produced by a known method (Example 1 of JP-B 2669554) by physical adsorption.

150 g of the resultant separating agent (ratio at which a polymer was supported: 20 wt %) were suspended in 3 L of the mixed solvent of water and acetonitrile, and the suspension was stirred. The suspension was irradiated with UV for 220 minutes by a method described in Example 12 of JP 11-510193 A so that crosslinking might take place. After that, the resultant solids were taken out by filtration, repeatedly washed with tetrahydrofuran under heat and reflux 4 times, and dried in a vacuum, whereby a target enantiomeric isomer separating agent was obtained.

A predetermined liquid passing test was performed by using the enantiomeric isomer separating agent of the present invention and tetrahydrofuran as a solvent to determine the concentration of eluted component (ppm). As a result, the $M_1$ was 416.18 g, the $M_2$ was 2.7 mg, and the ratio $M_2/M_1$ was 6.5 ppm.

Comparative Example 1

An unwashed chemical support type enantiomeric isomer separating agent was obtained in the same manner as in Example 1. 100 g of the resultant separating agent were washed by a general washing method. That is, the separating agent was filtrated through a glass filter at room temperature, and was washed with 2.4 L of methanol.

A liquid passing test of the present invention was performed by using the resultant enantiomeric isomer separating agent and ethyl acetate as a solvent to determine the concentration of eluted component. The $M_1$ was 416.15 g, the $M_2$ was 85 mg, and the ratio $M_2/M_1$ was 204 ppm.

Comparative Example 2

An unwashed chemical support type enantiomeric isomer separating agent was obtained in the same manner as in Example 2. 100 g of the resultant separating agent were washed by a general washing method. That is, the separating agent was filtrated through a glass filter at room temperature, and was washed with 2.4 L of methanol.

A liquid passing test of the present invention was performed by using the resultant enantiomeric isomer separating agent and THF as a solvent to determine the concentration of eluted component. The $M_1$ was 416.23 g, the $M_2$ was 203 mg, and the ratio $M_2/M_1$ was 488 ppm.

What is claimed is:

1. A method of producing an enantiomeric isomer separating agent comprising a polysaccharide derivative supported on particles of a support by chemical bonding and having a concentration of eluted component, in terms of mass proportion, of no more than 20 ppm, said method comprising the steps of:

washing an enantiomeric isomer separating agent comprising the polysaccharide derivative supported on particles of a support by chemical bonding and having a concentration of eluted component, in terms of mass proportion, of greater than 20 ppm, at least once with an organic solvent in which the polysaccharide derivative is soluble, the organic solvent being at a temperature of from 50-150° C. and selected from the group consisting of tetrahydrofuran, acetone, ethyl acetate, methylene chloride, dimethylacetamide and dimethylformamide for a period of from 1-100 hours and drying the washed enantiomeric isomer separating agent, wherein the concentration of eluted component is determined by a liquid passing test comprising the steps of:

packing the enantiomeric isomer separating agent in a column having a diameter of 1 cm and a length of 25 cm by a slurry method;

passing the organic solvent in which the polysaccharide derivative is soluble in and at a temperature of 40° C. through the enantiomeric isomer separating agent in the column at a flow rate of 8 ml/min and forming an eluate;

initiating the collection of the eluate one hour after initiating the passing of the solvent through the enantiomeric isomer separating agent in the column and measuring the mass, $M_1$, of the eluate collected;

condensing and drying the collected eluate and measuring the mass, $M_2$, of remaining residue; and determining the concentration of the eluent component from the expression $M_2/M_1$.

2. The method of claim 1, wherein the polysaccharide derivative is a cellulose derivative or an amylose derivative and the support is silica gel.

3. The method of claim 1, wherein 5-100 ml of organic solvent per gram of polysaccharide derivative in the enantiomeric isomer separating agent is used in the washing step.

4. The method of claim 1, wherein the organic solvent is at a temperature of 70-100° C. during the washing step.

5. The method of claim 1, wherein the enantiomeric isomer separating agent is washed from 2-10 times with the organic solvent.

6. The method of claim 1, wherein said organic solvent is acetone, the polysaccharide derivative is cellulose tris (3,5-dimethylphenylcarbamate) and the support is silica.

7. The method of claim 1, wherein said organic solvent is selected from the group consisting of dimethylformamide and tetrahydrofuran, the polysaccharide derivative is selected from the group consisting of amylose tris (3,5-dimethylphenylcarbamate) and cellulose tris (3,5-dimethylphenylcarbamate) and the support is silica.

\* \* \* \* \*